United States Patent [19]

Ifuku

[11] Patent Number: 5,297,037
[45] Date of Patent: Mar. 22, 1994

[54] X-RAY SIMULATING METHOD AND SYSTEM FOR RADIOTHERAPY PLAN

[75] Inventor: Akira Ifuku, Ootawara, Japan

[73] Assignee: Kabushiki Kaisha Toshiba, Kawasaki, Japan

[21] Appl. No.: 738,558

[22] Filed: Jul. 31, 1991

[30] Foreign Application Priority Data

Jul. 31, 1990 [JP] Japan .................................. 2-203547

[51] Int. Cl.$^5$ ......................... A61N 5/10; A61B 6/00
[52] U.S. Cl. .................................. 364/413.15; 378/65; 378/152
[58] Field of Search .................. 378/6, 4, 18, 46, 65; 364/413.13, 413.14, 413.22

[56] References Cited

U.S. PATENT DOCUMENTS

| | | | |
|---|---|---|---|
| 4,922,915 | 5/1990 | Arnold et al. | 128/653 R |
| 4,943,990 | 7/1990 | Schär | 378/152 |
| 5,014,290 | 5/1991 | Moore et al. | 378/145 |
| 5,022,060 | 6/1991 | Trotel | 378/19 |
| 5,027,818 | 7/1991 | Bova et al. | 128/653 R |
| 5,081,984 | 1/1992 | Wess et al. | 128/24 EC |
| 5,099,505 | 3/1992 | Seppi et al. | 378/65 |
| 5,123,056 | 6/1992 | Wilson | 382/6 |
| 5,132,996 | 7/1992 | Moore et al. | 378/65 |

*Primary Examiner*—Roy N. Envall, Jr.
*Assistant Examiner*—A. Bodendorf
*Attorney, Agent, or Firm*—Oblon, Spivak, McClelland, Maier & Neustadt

[57] ABSTRACT

An X-ray simulating system for a radiotherapy planning disclosed by this invention includes an acquiring unit for acquiring an image showing a diseased part, a detecting unit for detecting the shape of the diseased part on the basis of the image acquired by the image acquiring unit, a calculating unit for calculating simulation data for radiation on the basis of first data including data related to the shape of the diseased part detected by the detecting unit and second data including data related to radiation conditions in radiotherapy, and a supplying unit for supplying the simulation data calculated by the calculating unit to a radiation therapy apparatus.

7 Claims, 7 Drawing Sheets

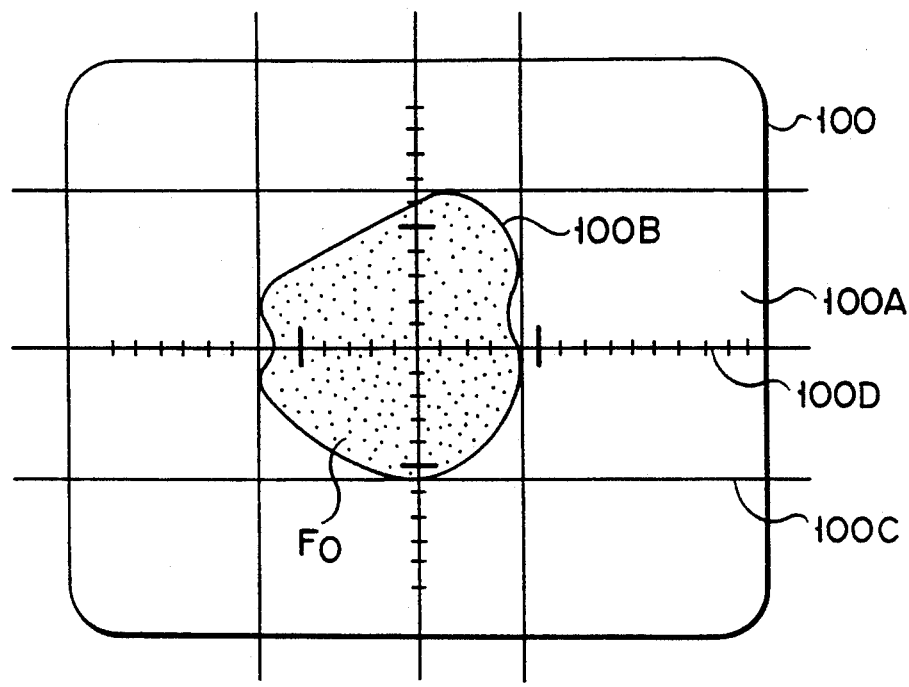
F I G. 4
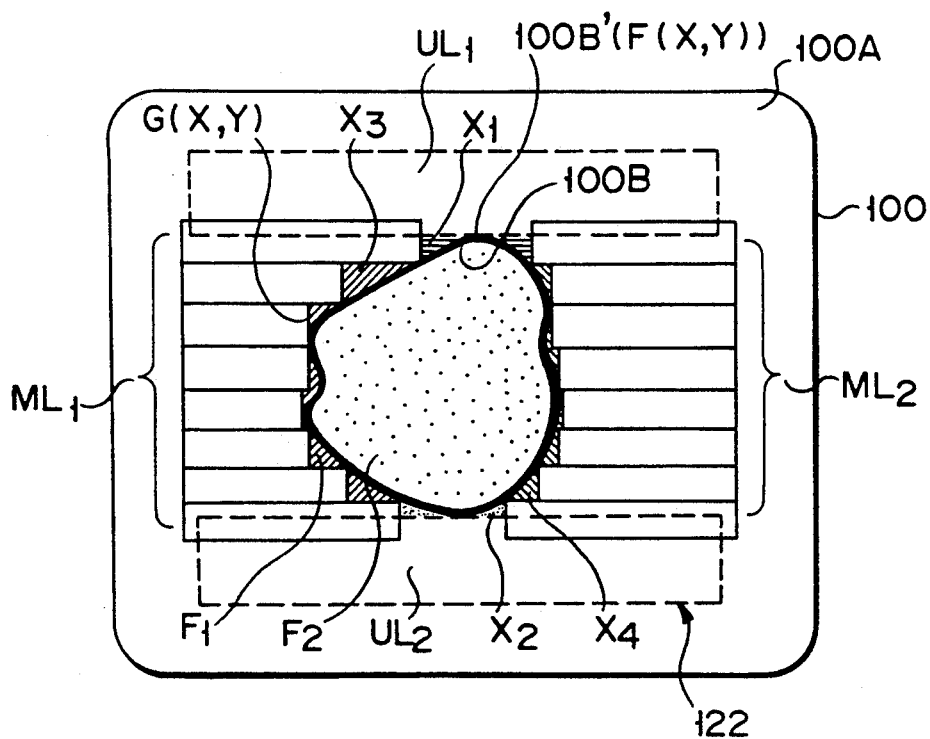
F I G. 5

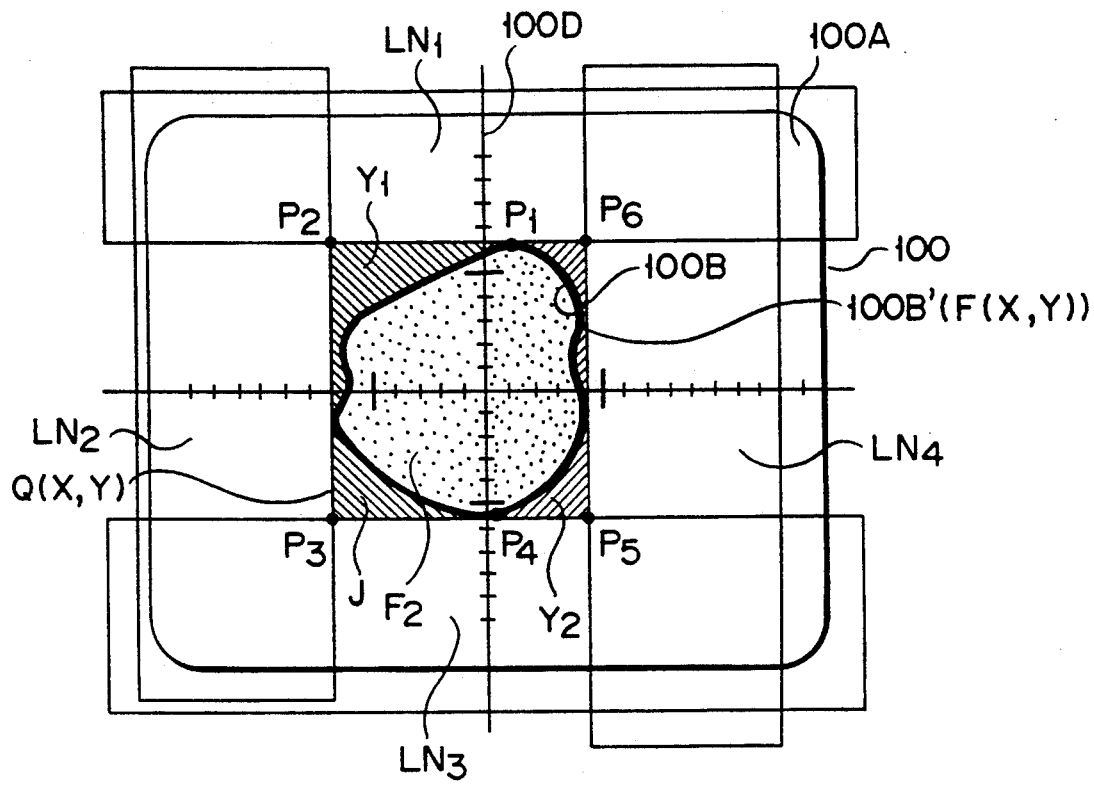
F I G. 7
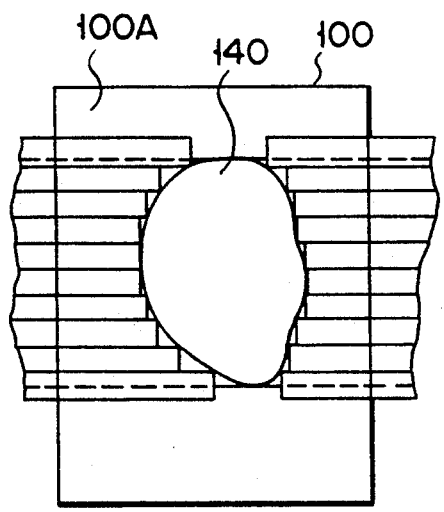
F I G. 10A
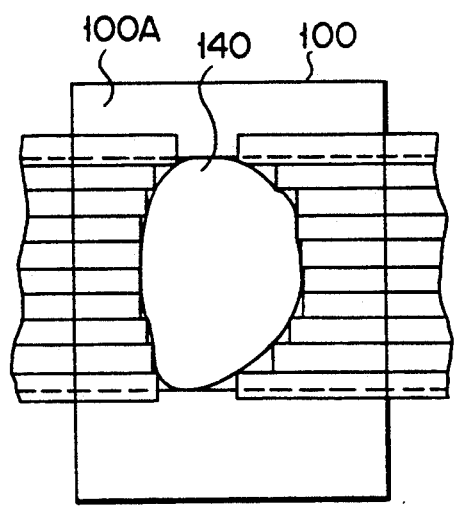
F I G. 10B

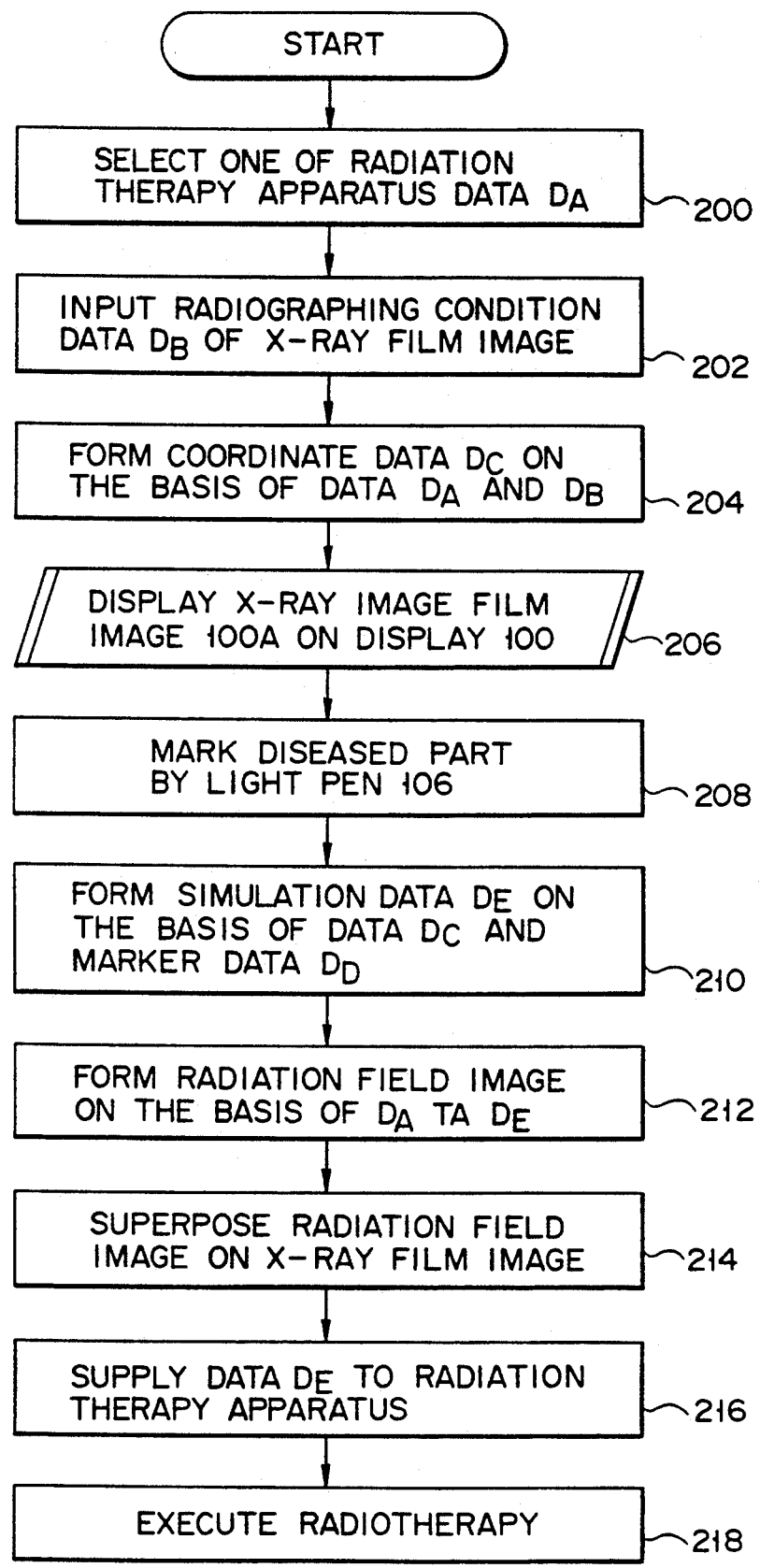
F I G. 8

X-RAY SIMULATING METHOD AND SYSTEM FOR RADIOTHERAPY PLAN

BACKGROUND OF THE INVENTION

1. Field of the Invention

The present invention relates to an X-ray simulating method and system for a radiotherapy planning for obtaining radiotherapy simulation data.

2. Description of the Related Art

In radiotherapy, generally, a therapy planning is made prior to execution of the therapy, and the therapy is executed on the basis of the therapy planning to obtain effective clinical results. Such a radiotherapy planning essentially includes at least a process of acquiring correct geometrical information concerning a diseased part (focus) and a process of determining proper radiation conditions on the basis of the geometric information (a radiotherapy simulation data determination process).

A typical example of an apparatus for use in the radiotherapy planning is an X-ray simulator, and an X-ray simulator of this type is basically an X-ray imaging apparatus. A conventional X-ray simulator will be described below with reference to FIG. 1.

As shown in FIG. 1, this conventional X-ray simulator is an apparatus capable of setting an X-ray tube 10 and an X-ray image acquiring unit 20 at desired positions where they oppose each other with a patient 30 sandwiched therebetween. The X-ray generator 10 comprises an X-ray tube 12 and a limiting unit 14. The limiting unit 14 is constituted by at least an X-ray diaphragm, a simulation collimator (wire collimator) and a simulation scale.

The X-ray image acquiring unit 20 generally comprises a system for acquiring a fluoroscopic image and a system for acquiring a radiographic image. The fluoroscopic image is a TV image used as a positioning image for confirming a position for radiographing an X-ray film image. The radiographic image is an X-ray film image used as an image for obtaining geometrical data of a diseased part. Images of a diseased part 32, the wire collimator, and the simulation scale are formed on the X-ray film image. Note that the patient 30 is placed on a tabletop 40.

The X-ray generator 10 and the X-image acquiring unit 20 of the X-ray simulator are set to oppose each other in POSITION "A" as shown in FIG. 1, and an X-ray film image 50 of a patient at POSITION "A" is acquired while a fluoroscopic image is observed. Subsequently, the X-ray generator 10 and the X-ray acquiring unit 20 of the X-ray simulator are set to oppose each other in POSITION "B" as shown in FIG. 1, and a radiographic image (X-ray film image) 52 of the patient 30 at POSITION "B" is acquired while the fluoroscopic image is observed. The X-ray radiation directions are different from each other by a predetermined angle such as 90° at POSITION "A" and POSITION "B".

On the X-ray film image 50 acquired at POSITION "A", a diseased part image 50A, an image of a portion except for the diseased part, and reference images such as a wire collimator image 50B and a simulation scale image 50C are formed. On the X-ray film image 52 acquired at POSITION "B", a diseased part image 52A, an image of a portion except for the diseased part, and reference images such as a wire collimator image 52B and a simulation scale image 52C are formed.

An operator obtains geometrical information of the diseased part 32 by observing the X-ray film images 50 and 52 while referring to the fluoroscopic images at POSITION "A" and POSITION "B". In this case, the operator observes the X-ray film images 50 and 52 by associating the diseased part images 50A and 52A, the images of the portion except for the diseased part, and the reference images such as the wire collimator images 50B and 52B and the simulation scale images 50C and 52C, respectively formed on the X-ray film images 50 and 52, with one another.

On the basis of the geometrical information of the diseased part 32, the operator forms simulation data for radiotherapy, which determines radiation conditions such as the type, the radiation field, and the radiation direction of rays for use in the therapy. This simulation data is supplied to a radiation therapy apparatus such as Linear accelerator, and the radiation therapy apparatus executes radiotherapy on the basis of the input simulation data.

As described above, the X-ray simulator used in a conventional radiotherapy plan simply provides X-ray film images for obtaining geometrical information of a diseased part. An operator obtains geometrical information of a diseased part from the X-ray film images and forms radiotherapy simulation data on the basis of the geometrical information of the diseased part. The operator forms the radiotherapy simulation data for determining radiation conditions by manually operating an instrument such as the limiting unit 14 of the X-ray simulator or an instrument such as a limiting unit of a radiation therapy apparatus, or by manually operating a patient table of the X-ray simulator or that of the radiation therapy apparatus.

This manual operation is constituted by a plurality operations. Therefore, formation of the radiotherapy simulation data is difficult and incorrect. For example, a limiting aperture is determined by the eye on the basis of geometrical information of a diseased part. Therefore, a trial-and-error operation must be performed a large number of times to determine an optimal radiation field capable of minimizing a radiation dose to a normal part of a patient. If the number of operation times is small, on the other hand, the operation precision is degraded.

SUMMARY OF THE INVENTION

It is, therefore, an object of the present invention to provide an X-ray simulating method and system for a radiotherapy planning, which can easily form radiotherapy simulation data with high precision.

The above object of the present invention is achieved by an X-ray simulating system for a radiotherapy planning, comprising:

acquiring means for acquiring an image showing a diseased part;

detecting means for detecting a shape of the diseased part on the basis of the image acquired by the image acquiring means;

calculating means for calculating simulation data for radiation on the basis of first data including data related to the shape of the diseased part detected by the detecting means and second data including data related to radiation conditions in radiotherapy; and supplying means for supplying the simulation data calculated by the calculating means to a radiation therapy apparatus.

In addition, the above object of the present invention is achieved by an X-ray simulation system for a radiotherapy planning, comprising:

an X-ray simulator for radiographing an X-ray film image showing a diseased part;

marking means for marking a shape of the diseased part on the basis of the X-ray film image radiographed by the X-ray simulator;

calculating means for calculating simulation data, including limiting aperture data and limiting rotational angle data for defining a radiation field with which a radiation dose to a normal part of a patient is minimized, on the basis of the data related to the shape of the diseased part marked by the marking means and specification data of a limiting unit included in a radiation therapy apparatus; and supplying means for supplying the simulation data calculated by the calculating means to the radiation therapy apparatus.

Furthermore, the above object of the present invention is achieved by an X-ray simulating method for a radiotherapy planning, comprising:

the acquiring step of acquiring an image showing a diseased part;

the detecting step of detecting a shape of the diseased part on the basis of the image acquired by the image acquiring step;

the calculating step of calculating simulation data for radiation, for defining a radiation field with which a radiation dose to a normal part of a patient is minized, on the basis of first data related to the shape of the diseased part detected by the detecting step and second data related to radiation conditions in radiotherapy; and the supplying step of supplying the simulation data calculated by the calculating means to the radiation therapy apparatus.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 4 is a view showing setting of coordinate data;

FIG. 5 is a view for explaining a method of calculating a radiation field in a multiple-partition limiting device;

FIG. 7 is a view for explaining a method of calculating a radiation field in a mono-block limiting device;

FIG. 8 is a flow chart for explaining an X-ray simulating method for a radiotherapy plan according to the present invention;

FIGS. 10A and 10B are views for explaining a method of calculating a radiation field in a horizontally symmetrical diseased part.

DETAILED DESCRIPTION OF THE PREFERRED EMBODIMENTS

Figure 1:
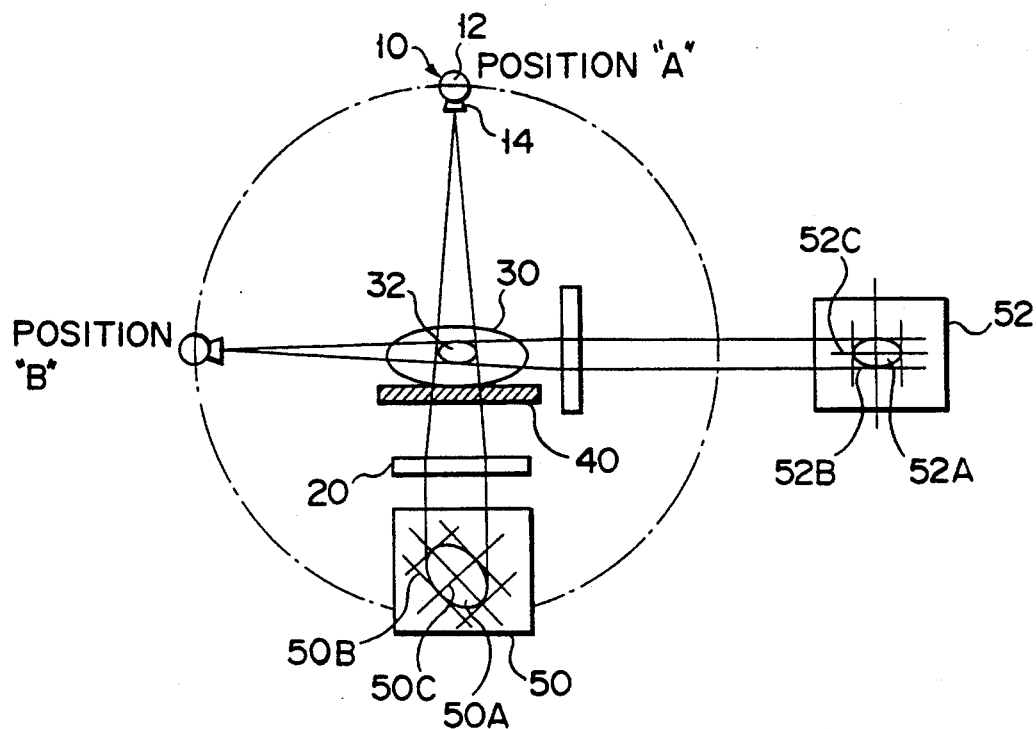
FIG. 1 is a schematic view showing a conventional radiotherapy planning system.

An embodiment of the present invention will be described below with reference to the accompanying drawings.

An X-ray simulating method and system for a radiotherapy planning according to an embodiment of the present invention comprise an X-ray simulator and electric devices.

The X-ray simulator in the X-ray simulating system will be described with reference to FIG. 2. That is, a rotary gantry 64 is pivotally mounted on a fixed gantry 62 fixed on a floor 60. Upper and lower support arms 66 and 68 are mounted on the rotary gantry 64 so as to be movable in the longitudinal direction of the gantry 64. A patient table 70 for placing a patient 30 thereon is spatially sandwiched between the upper and lower support arms 66 and 68. The table 70 has a tabletop 72.

An X-ray generator 74 is mounted on the upper support arm 66. The X-ray generator 74 includes an X-ray tube 76 and a limiting unit 78 for determining an X-ray radiation field. The limiting unit 78 is constituted by an X-ray diaphragm, a simulation collimator (wire collimator), and a simulation scale.

An X-ray image acquiring unit 80 is mounted on the lower support arm 68 so as to oppose the limiting unit 78. The X-ray image acquiring unit 80 has a fluoroscopic image acquiring system 82 constituted by an image intensifier and a TV camera, and a radiographic image acquiring system 84 constituted by an X-ray film changer.

Figure 2:
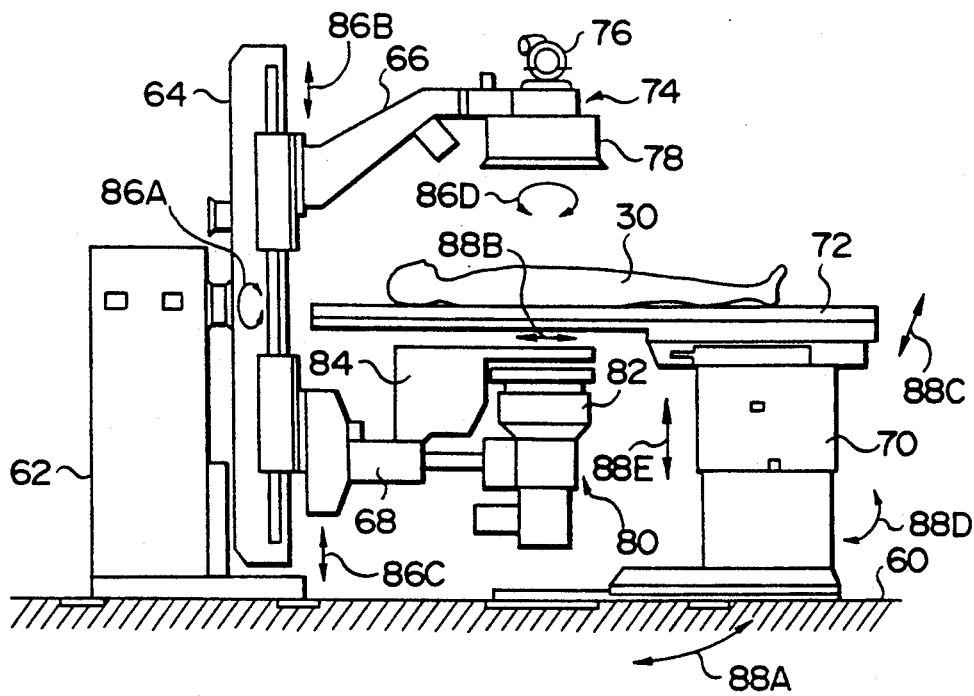
FIG. 2 is a front view showing an embodiment of an X-ray simulator usable in the present invention.

The X-ray simulator performs a rotary gantry rotation, an SAD (source-to-axis distance) varying motion, an AID (axis-to-image intensifier distance) varying motion, and a limiting unit rotation respectively denoted by reference symbols 86A, 86B, 86C, and 86D in FIG. 2. The patient table 70 performs an isocentric rotation, a tabletop forward-to-backward motion, a tabletop left-to-right motion, a tabletop rotation, and a tabletop vertical motion respectively denoted by reference symbols 88A, 88B, 88C, 88D, and 88E in FIG. 2.

According to the X-ray simulator having the above arrangement, X-ray fluoroscopic images and X-ray film images can be obtained in two orthogonal directions with respect to a patient. An operator can check geometrical features of a diseased part such as the spread and the depth of a diseased part by observing these images. First, the operator can recognize geometrical features such as the position and the direction of a diseased part and the shape of a radiation field by the fluoroscopic images. Thereafter, the operator can check the geometrical features of the diseased part also by observing the X-ray film images. As is the case with the arrangement shown in FIG. 1, a diseased part image, an image of a portion except for a diseased part, and reference images such as a simulation collimator (wire collimator) image and a simulation scale image are simultaneously formed on the X-ray film image.

Figure 3:
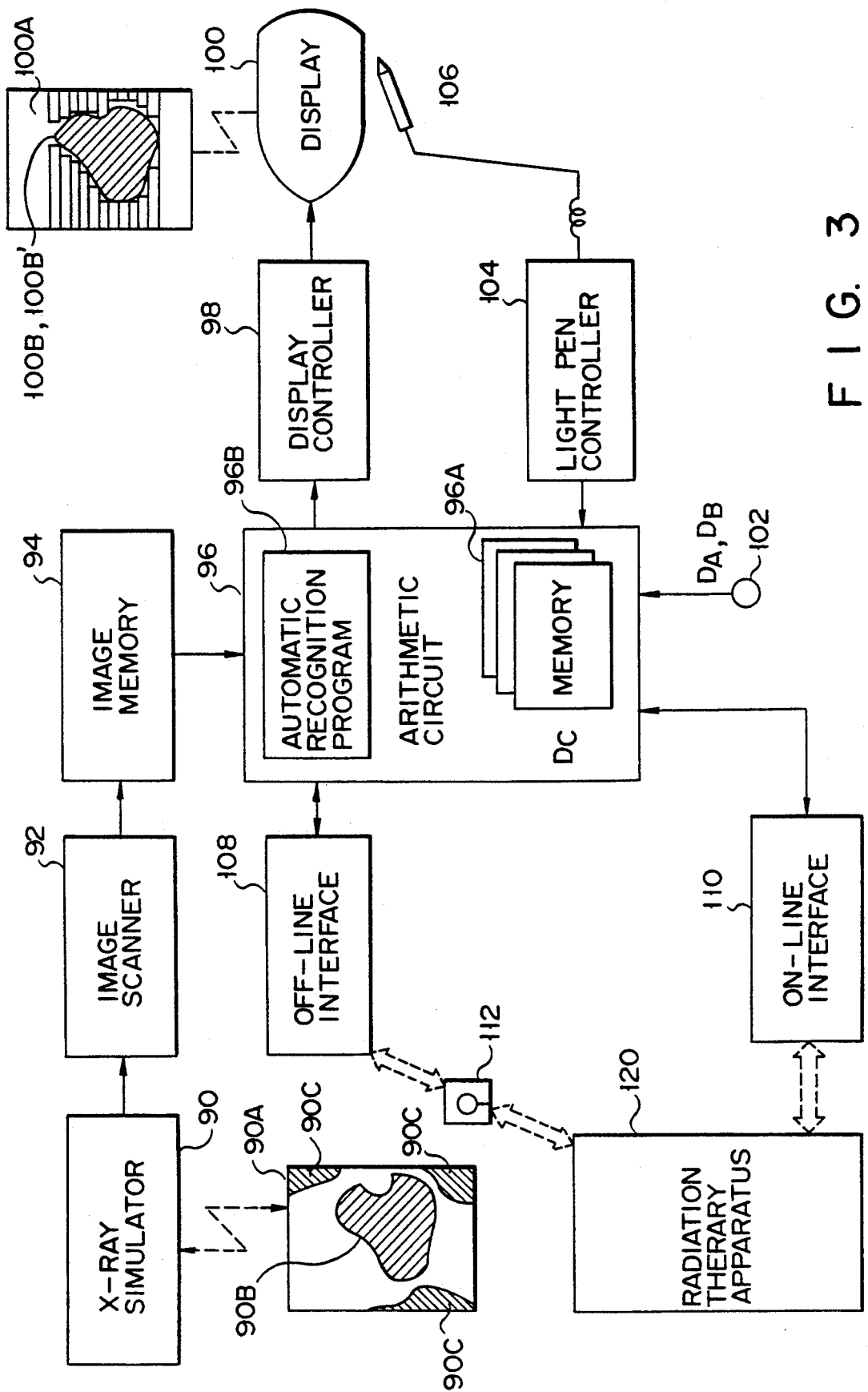
FIG. 3 is a block diagram showing an X-ray simulating system for a radiotherapy plan according to the present invention.
Figure 6A:
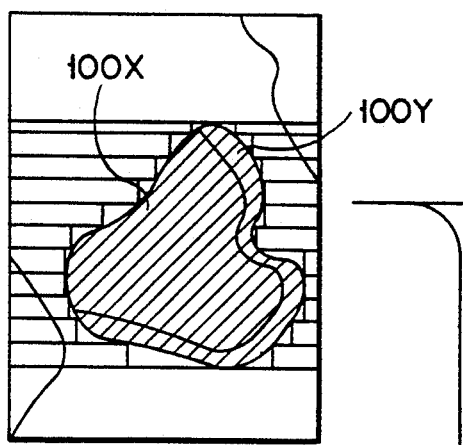
FIGS. 6A to 6D are views for explaining another method of calculating a radiation field in the multiple-partition limiting device.
Figure 6B:
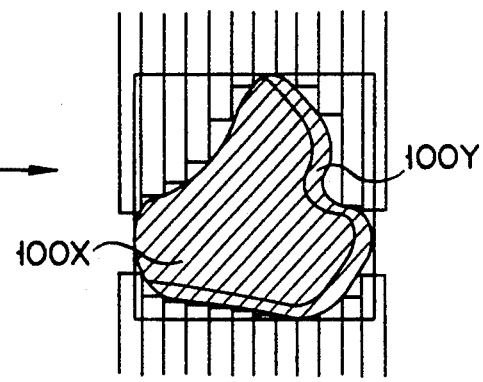
Figure 6C:
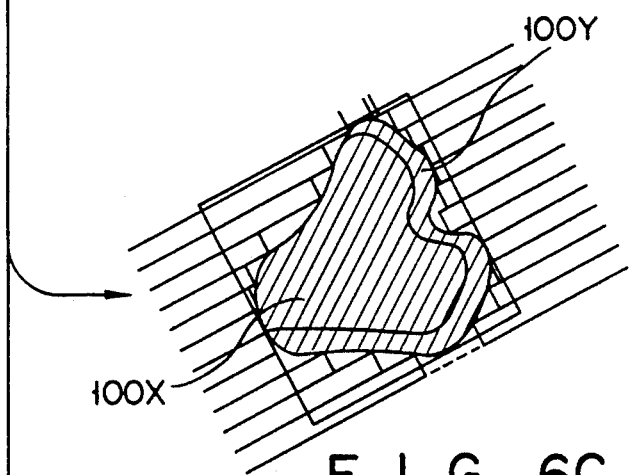
Figure 6D:
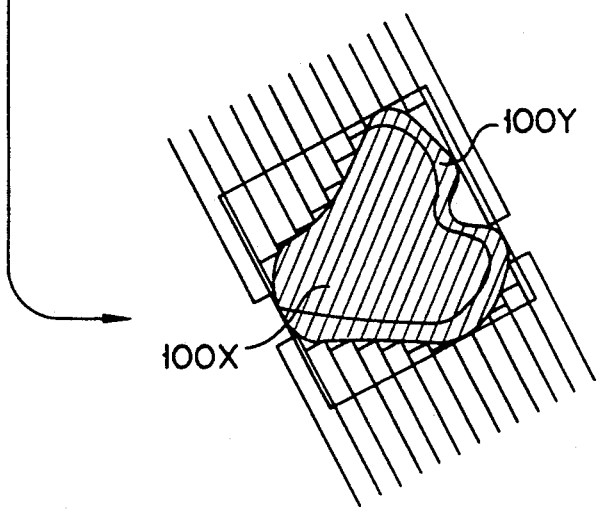

The electric devices used in the X-ray simulating system will be described below with reference to FIG. 3. Referring to FIG. 3, a simulator 90 is typically the X-ray simulator shown in FIG. 2. However, an ordinary visual apparatus except for the X-ray simulator shown in FIG. 2, such as an X-ray imaging apparatus, or an X-ray CT scanner apparatus can be used. In the following description, the simulator 90 will be explained as the X-ray simulator shown in FIG. 2.

The X-ray simulator 90 provides an X-ray film image 90A showing a diseased part. This X-ray film image 90A includes at least a diseased part image 90B, images 90C of portions except for the diseased part, and reference images (not shown) such as a simulation collimator (wire collimator) image and a simulation scale image. An image scanner 92 receives the X-ray film image 90A. Therefore, the image scanner 92 outputs a digitally formatted X-ray film image by an electrical signal. The digitally formatted X-ray film image is stored in an image memory 94. A digitizer can be used in place of the image scanner 92.

The X-ray film image is displayed on a display 100 such as a cathode-ray tube via an arithmetic circuit 96 and a display controller 98. Similar to the original X-ray film image 90A, an X-ray film image 100A displayed on the display 100 includes at least a diseased part image 100B, an image (not shown) of a portion except for a diseased part, and reference images (not shown) such as a simulation collimator (wire collimator) image and a simulation scale image.

The arithmetic circuit 96 is a device for performing processing operations which are characteristic features of the present invention. The arithmetic circuit 96 has an internal memory 96A and an automatic recognition program 96B. The memory 96A is used to store several useful data. The memory 96A stores a plurality of radiation therapy apparatus data $D_A$. The data $D_A$ indicates types of one or a plurality of radiation therapy apparatuses and specifications of the radiation therapy apparatuses such as arrangements of limiting units of the apparatuses. The limiting unit of the radiation therapy apparatus expressed by the data has at least a multiple-partition limiting device or a mono-block limiting device. For the multiple-partition limiting device, an aperture scale, the number of limiting partitions, and the width of a limiting partition are the contents of the radiation therapy apparatus data $D_A$. The data $D_A$ is input to the arithmetic circuit 96 from a data input device 102 such as a keyboard connected to the arithmetic circuit 96 and is stored in the memory 96A. The data input device 102 is used to input radiographing condition data $D_B$.

The radiographing condition data $D_B$ contains main-body information such as the X-ray radiation direction, the X-ray dose, the magnification, the rotary gantry rotation, the SAD varying motion, the AID varying motion, and the limiting unit rotation set when an X-ray film image is radiographed, and patient-table information such as the isocentric rotation, the tabletop forward-to-backward motion, the tabletop right-to-left motion, the tabletop rotation, and the tabletop vertical motion set when the X-ray film image is radiographed.

On the basis of the radiation therapy apparatus data $D_A$ and the radiographing condition data $D_B$, coordinate data $D_C$ indicating conditions for matching the coordinates of the X-ray simulator and those of the radiation therapy apparatus is obtained. Formation of the data $D_C$ is performed by the arithmetic circuit 96. In the coordinate data $D_C$, the X axis is defined as an aperture scale of the multiple-partition limiting device of the radiation therapy apparatus, and the Y axis is defined as a width scale of one limiting partition of the multiple-partition limiting device of the apparatus. When the radiographing condition data $D_B$ is input, the coordinate data is calculated on the basis of the radiographing condition data $D_B$ and the radiation therapy apparatus data $D_A$. The coordinate data $D_C$ is also stored in the memory 96A. The coordinate data $D_C$ is considered as data obtained by processing the coordinates of the X-ray simulator by a predetermined transformer or a practical arithmetic method so as to correspond to the coordinates of the radiation therapy apparatus.

A light pen 106 controlled by a light pen controller 104 marks the diseased part 100B shown in the X-ray film image 100A displayed on the display 100. An operator holds the light pen 106 and traces a portion of interest on the display 100 with the distal end of the light pen 106, thereby achieving the above marking operation. In this embodiment, the "marking" is to surround the diseased part 100B with a line drawn along the edge of the diseased part. The line drawn to surround the diseased part 100B by marking is input as marker data $D_D$ to the arithmetic circuit 96. The marker data $D_D$ is represented by a function F (x,y) defined Diseased part outline data is obtained by the automatic recognition program 96B of the arithmetic circuit 96. This diseased part outline data corresponds to the marker data $D_D$ obtained by marking.

The arithmetic circuit 96 forms data DE on the basis of the coordinate data $D_C$ and the marker data $D_D$ (or the diseased part outline data). In addition, the arithmetic circuit 96 forms marker image data on the basis of the marker data $D_D$. A marker image 100B' is displayed on the display 100 on the basis of the marker image data. This marker image 100B' coincides with the line surrounding the diseased part 100B obtained by marking. That is, the locus of the distal end of the light pen 106 on the display 100 is displayed as the marker image on the display 100.

The simulation data $D_E$ is constituted by a plurality of data. At least one data of the simulation data $D_E$ indicates position information (limiting aperture data) of each limiting partition of the limiting unit, with which the end portion of each limiting partition of the limiting unit (multiple-partition limiting device) contacts the marker line represented by the function F (x,y) and an area between the marker line and the end portion of each limiting partition of the limiting unit (multiple-partition limiting device) is minimized. Minimization of the area achieves minimization of a radiation dose to a normal part of a patient.

A method of calculating the limiting aperture data as one data of the simulation data $D_E$ will be described below with reference to FIGS. 4, 5, and 6.

FIG. 4 is a schematic view showing the X-ray film image 100A displayed on the display 100. No marking is performed in the stage shown in FIG. 4. The diseased part 100B and reference images C are shown in the X-ray film image 100A. The reference images C include a simulation collimator (wire collimator) image and a simulation scale image (neither are shown). Simulation coordinates are set on this X-ray film image 100A.

Setting of the simulation coordinates may be either automatically performed by the arithmetic circuit 96 on the basis of the coordinate data $D_C$ or manually performed by an operator by operating the data input device 102. The simulation coordinates thus automatically or manually set are visualized. A simulation coordinate image 100D obtained in this manner can be displayed in the X-ray film image 100A on the display 100. In this case, a plurality of display forms are available. In the first form, the X-ray film image 100A and the simulation coordinate image 100D are superposed and displayed on the displayed 100. In the second form, only the X-ray film image 100A is displayed on the display 100. In the third form, only the simulation coordinate image 100D is displayed on the display 100. FIG. 4 shows a display example according to the third form.

FIG. 5 shows a method of calculating the limiting aperture data as one data of the simulation data $D_E$ for a radiation therapy apparatus having the multiple-partition limiting device. FIG. 5 is a schematic view showing the X-ray film image 100A and the marker image 100B' displayed on the display 100. Marking is already performed in the stage shown in FIG. 5. The display 100 displays the marker image 100B' corresponding to the diseased part image 100B. As described above, the marker image 100B' is defined by the simulation coordinates based on the coordinate data $D_C$. A multiple-partition limiting device 122 expressed by data comprises upper limiting partitions UL1 and UL2 and side limiting partition groups ML1 ML2.

The X-ray film image 100A and the marker image 100B' are displayed on the display 100. The arithmetic circuit 96 calculates, on the basis of the radiation therapy apparatus data $D_A$, coordinate data for the multiple-partition limiting device, with which the end portion of each limiting partition of the multiple-partition limiting device contacts the marker line (marker image 100B').

Assume that the above coordinate data for the multiple-partition limiting device is G (x,y). The line defined by G (x,y) represents the end portions of the respective limiting partitions of the multiple-partition limiting device. G (x,y) forms a step-like line in FIG. 5 and can be arbitrarily changed. Assume that an area in the step-like line formed by G (x,y) is F1.

The marker data $D_D$ is the function F (x,y). The function F (x,y) forms a curve and is fixed.

F3 (X1+X2+X3+X4) is obtained by subtracting an area F2 in the curve corresponding to the diseased part from the area F1 in the step-like line formed by the end portions of the respective limiting partitions. X1 represents a region surrounded by the side of the upper limiting partition UL1 and the function F (x,y); X2, a region surrounded by the upper limiting partition UL2 and the function F (x,y); X3, a region surrounded by the end portion sides of the plurality of side limiting partitions ML1 and the function F (x,y); and X4, a region surrounded by the end portion sides of the plurality of side limiting partitions ML2 and the function F (x,y). To minimize F3 is to minimize the radiation dose to a normal part of a patient. In order to minimize F3, G (x,y) must approximate F (x,y) with a minimum error. This approximating method is realized by a general numerical analysis program.

FIG. 5 shows the method of calculating the limiting aperture data as one data of the simulation data $D_E$ when the axes of x and y coordinates of the X-ray film image 100A and those of the multiple-partition limiting device 122 (UL1, UL2, ML1, and ML2) coincide with each other. This method is based on the assumption that the limiting unit of the radiation therapy apparatus is fixed. The limiting unit of the radiation therapy apparatus, however, can be either fixed or rotated. FIGS. 6A, 6B, 6C, and 6D show a method of calculating the limiting aperture data as one data of the simulation data $D_E$ when the limiting unit of the radiation therapy apparatus is both fixed and rotated. Even when the limiting unit is rotated, the limiting aperture data as one data of the simulation data $D_E$ can be calculated in the same manner as when the limiting unit is fixed, although the coordinate data $D_C$ is different between the two cases. Note that FIGS. 6A to 6D show a diseased part image 100X obtained by marking and a diseased part automatic recognition image 100Y obtained by executing the automatic recognition program 96B.

FIG. 7 shows a method of calculating the limiting aperture data as one data of the simulation data $D_E$ for a radiation therapy apparatus having a mono-block limiting device. FIG. 7 is a schematic view showing the X-ray film image 100A and the marker image 100B' displayed on the display 100. Marking is already performed in the stage shown in FIG. 7. A mono-block limiting device 124 expressed by data comprises four limiting partitions LN1, LN2, LN3, and LN4. The display 100 displays the marker image 100B' corresponding to the diseased part image 100B.

The X-ray film image 100A and the marker image 100B' are displayed on the display 100. The arithmetic circuit 96 calculates, on the basis of the radiation therapy apparatus data $D_A$, coordinate data for the mono-block limiting device, with which the end portion of each of the limiting partitions LN1, LN2, LN3, and LN4 of the mono-block limiting device 124 contacts the marker line (marker image 100B').

Assume that the above coordinate data for the mono-block limiting device is Q (x,y). The line defined by Q (x,y) represents the end portions of the respective limiting partitions LN1, LN2, LN3, and LN4 of the mono-block limiting device 124. Q (x,y) forms a rectangular region in FIG. 6 and can be arbitrarily changed. Assume that an area in the rectangular region formed by Q (x,y) is J.

The marker data $D_D$ is the function F (x,y). The function F (x,y) forms a curve and is fixed.

Y (Y1+Y2) is obtained by subtracting an area F2 in the curve corresponding to the diseased part from the area J in the rectangular region formed by the end portions of the respective limiting partitions LN1, LN2, LN3, and LN4 of the mono-block limiting device 124. Y1 represents a region surrounded by the side of the upper limiting partition LN1, the side of the left limiting partition LN2, the side of the lower limiting partition LN3, and the function F (x,y); and Y2, a region surrounded by the side of the upper limiting partition LN1, the side of the right limiting partition LN4, the side of the lower limiting partition LN3, and the function F (x,y). To minimize Y (Y1+Y2) is to minimize radiation dose to a normal part of a patient. In order to minimize Y (Y1+Y2), Q (x,y) must approximate F (x,y) with a minimum error. This approximating method is realized by a general numerical analysis program.

Other data of the simulation data $D_E$ calculated by the arithmetic circuit 96 are data defining radiation conditions such as the radiation direction and the radiation dose in the therapy. The arithmetic circuit 96 also forms a radiation field image by the data $D_E$. The radiation field image is superposed on the X-ray film image 100A.

The simulation data $D_E$ is supplied to an off-line interface 108 and an on-line interface 110. The off-line interface 108 is an external memory device such as a floppy disk driver, which writes the data $D_E$ in a recording medium 112 such as a floppy disk. The recording medium 112 is supplied to a radiation therapy apparatus 120. The on-line interface 110 is a data transfer device. The data $D_E$ is supplied to the radiation therapy apparatus 120 via the on-line interface 110. The data $D_E$ formed by the simulating system shown in FIG. 3 is equivalent to operation data of the radiation therapy apparatus 120. That is, the system shown in FIG. 3 simulates the radiation therapy apparatus 120. Upon receiving the data $D_E$, the radiation therapy apparatus 120 performs radiotherapy on the basis of the data $D_E$.

The above simulating system shown in FIG. 3 operates in accordance with a flow chart shown in FIG. 8. In step 200 in FIG. 8, an operator operates the data input device 102 to select one of the radiation therapy apparatus data $D_A$. A radiation therapy apparatus to be used is determined by this selection. Assume that the selected radiation therapy apparatus has a multiple-partition limiting device as a limiting unit. This step is of course unnecessary if there is no other choice but one radiation therapy apparatus and a device such as a limiting unit incorporated in the apparatus has only one specification.

In step 202, the operator operates the data input device 102 to input the radiographing conditions $D_B$ obtained when an X-ray film image is radiographed by the X-ray simulator 90.

In step 204, the arithmetic circuit 96 calculates the coordinate data $D_C$ on the basis of the radiation therapy apparatus data $D_A$ and the radiographing condition data $D_B$. This coordinate data $D_C$ indicates conditions for matching the coordinates of the X-ray simulator 90 with those of the radiation therapy apparatus to be used or expressed by data.

In step 206, the X-ray film image 100A is displayed on the display 100.

In step 208, marking is performed by the light pen 106 so as to surround a diseased part on the X-ray film image 100A. The arithmetic circuit 96 holds the marker data $D_D$. A marker image is superposed on the X-ray film image 100A on the display 100 on the basis of the marker data $D_D$.

In step 210, the arithmetic circuit 96 forms the simulation data $D_E$ on the basis of the coordinate data $D_C$ and the marker data $D_D$. Typical data of the simulation data is limiting aperture data and limiting rotation angle data. This limiting aperture data corresponds to the multiple-partition limiting device.

In step 212, the arithmetic circuit 96 forms a radiation field image on the basis of the simulation data $D_E$.

In step 214, the radiation field image is superposed on the X-ray film image 100A on the display 100 as needed.

In step 216, the simulation data $D_E$ is supplied to the selected radiation therapy apparatus 120 via either the off-line interface 108 and the floppy disk 112 or the on-line interface 110.

In step 218, the radiation therapy apparatus 120 performs radiotherapy on the basis of the simulation data $D_E$.

According to the simulating system of the present invention as described above, an operator need only operate the data input device 102 to select the radiation therapy apparatus data $D_A$, input the radiographing condition data $D_B$, and operate the light pen 106 to perform marking, and the simulation data $D_E$ suited to the radiation therapy apparatus 120 can be formed and supplied to the apparatus 120 by this simple operation. Since this simulation data $D_E$ is formed not by a trial-and-error operation as in conventional systems but by the method based on image recognition, the data precision is high.

Figure 9A:
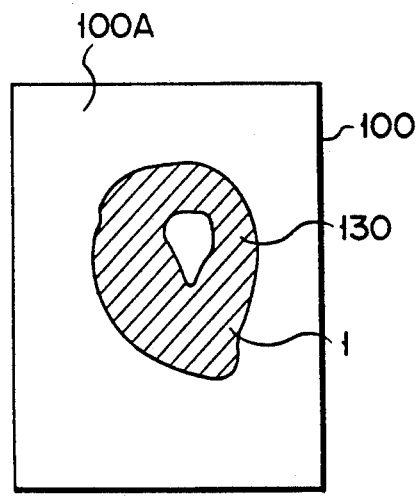
FIGS. 9A to 9C are views for explaining a method of calculating a radiation field in an annular diseased part.
Figure 9B:
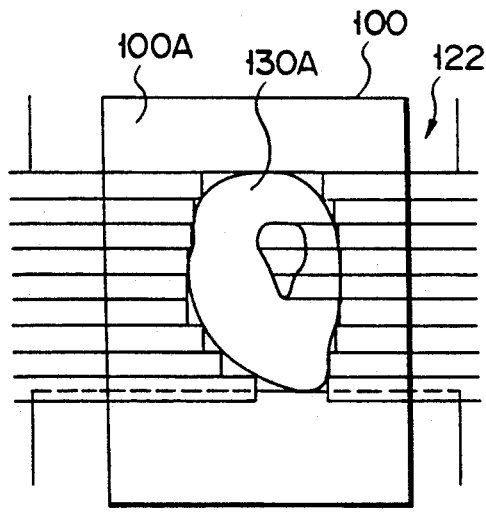
Figure 9C:
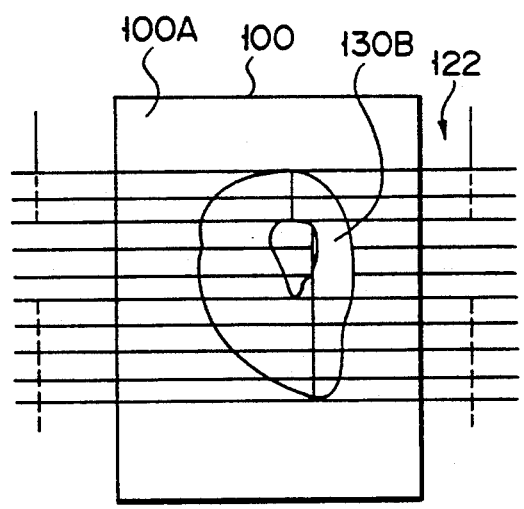

If a diseased part is like an annular diseased part 130 having an internal normal part or a valuable organ as shown in FIG. 9A, the simulation data $D_E$ can be formed by performing the method shown in FIG. 5 stepwise as shown in FIGS. 9B and 9C. That is, in the step shown in FIG. 9B, a partial diseased part 130A is recognized, and the simulation data $D_E$ is formed by the method shown in FIG. 5 using this partial diseased part 130A as marker data. Radiotherapy is partially performed on the basis of this simulation data $D_E$. In the step shown in FIG. 9C, a remaining diseased part 130B is recognized and used as marker data to form the simulation data $D_E$ by the method shown in FIG. 5, and the remaining radiotherapy is performed on the basis of this simulation data $D_E$. Radiotherapy for the entire diseased part 130 is achieved by this two-step radiotherapy.

In order to perform radiotherapy in two opposite directions, the simulation data $D_E$ for a diseased part shown on an X-ray film image radiographed from the front is formed, as shown in FIG. 10A. The simulation data $D_E$ for the side shown in FIG. 10B can be automatically calculated in consideration that a radiation field is horizontally symmetrical and geographically similar.

Note that marking can be performed by using, e.g., a track ball or mouse in place of the light pen 106.

Additional advantages and modifications will readily occur to those skilled in the art. Therefore, the invention in its broader aspects is not limited to the specific details, representative devices, and illustrated examples shown and described herein. Accordingly, various modifications may be made without departing from the spirit or scope of the general inventive concept as defined by the appended claims and their equivalents.

What is claimed is:

1. A system adapted to use a radiation therapy apparatus, for determining a radiation field in a radiotherapy of a patient, comprising:

acquiring means for acquiring an image showing a diseased region of the patient;

display means for displaying an image acquired by said acquiring means;

marking means for marking the shape of the diseased region in the image displayed on said display means;

determining means for determining data of the radiation field for radiation on the basis of first and second data, the first data being determined on the basis of radiation therapy apparatus data and image acquiring condition data of said acquiring means and expresses data related to the shape of the diseased region by coordinates of the radiation therapy apparatus on the basis of coordinate data for geometrically matching the coordinates of the radiation therapy apparatus with those of said acquiring means, the second data expressing a specification of a limiting unit included the radiation therapy apparatus; and supplying means for supplying the data of the radiation field determined by said determining means to the radiation therapy apparatus.

2. A system according to claim 1, wherein said acquiring means is an X-ray imaging devices for obtaining at least one of a fluoroscopic image and an X-ray film image.

3. A system according to claim 1, wherein said marking means is a light pen system.

4. A system according to claim 1, wherein the specification of said limiting unit of said radiation therapy apparatus is related to the number and the shape of limiting partitions of a multiple-portion limiting device.

5. A system according to claim 1, wherein the specification of said limiting unit of said radiation therapy apparatus is related to the number and the shape of limiting partitions of a monoblock limiting device.

6. A system according to claim 1, wherein said supplying means is an off-line interface for supplying the data of the radiation field to said radiation therapy apparatus.

7. A system according to claim 1, wherein said supplying means is an on-line interface for supplying the data of the radiation field to said radiation therapy apparatus.

* * * * *